United States Patent [19]

Binz et al.

[11] Patent Number: 5,601,799
[45] Date of Patent: Feb. 11, 1997

[54] PARTIALLY DELIPIDATED D25 POLYSACCHARIDE COMPOSITION FOR IMAGING AND DIAGNOSIS

[75] Inventors: Hans Binz, Beaumont; Lucien Dussourd D'Hinterland; Gérard Normier, both of Castres; Alain Le Pape, Langeais; Michel Favaron, St. Julien en Genevois; Souhail Delassan, Gaillard, all of France

[73] Assignee: Pierre Fabre Medicament, Boulogne, France

[21] Appl. No.: 369,430

[22] Filed: Jan. 6, 1995

Related U.S. Application Data

[63] Continuation of Ser. No. 192,833, Feb. 7, 1994, abandoned, which is a continuation of Ser. No. 54,347, Apr. 27, 1993, abandoned, which is a continuation of Ser. No. 666,805, Mar. 8, 1991, abandoned.

[30] Foreign Application Priority Data

Mar. 8, 1990 [FR] France ............................... 90 02957

[51] Int. Cl.$^6$ ....................... A61M 36/00; A61K 31/715; A61K 51/06
[52] U.S. Cl. .................. 424/1.73; 424/9.35; 424/9.6; 435/101; 530/322; 536/1.11; 536/4.1; 536/18.5; 536/119; 536/123; 536/18.7; 514/8; 514/54
[58] Field of Search ........................... 435/101; 424/1.73, 424/9.35, 9.6; 530/322; 536/1.1, 4.1, 18.5, 119, 123; 514/8, 54

[56] References Cited

U.S. PATENT DOCUMENTS

| | | | |
|---|---|---|---|
| 4,285,936 | 8/1981 | Pier et al. | 424/260.1 |
| 4,873,088 | 10/1989 | Mayhew et al. | 424/450 |
| 4,894,229 | 1/1990 | Polson et al. | 424/130.1 |
| 4,933,440 | 6/1990 | D'Hinterland et al. | 536/53 |
| 4,937,327 | 6/1990 | D'Hinterland et al. | 424/279.1 |

FOREIGN PATENT DOCUMENTS 0408444  1/1991  European Pat. Off. .

OTHER PUBLICATIONS

Acta Path, Microbiol. Scand, Section C, vol. 93, 1985, pp. 233–243, G. Normier et al., "NK–Cell Stimulating Properties of a Membrane Proteoglycane from Non–Capsulated Klebsiella Pneumoniae Biotype a".

Chemical Abstracts, vol. 108, No. 7, Feb. 15, 1988, Columbus, Ohio, Abstract 487265, Sinilova N. G. et al., "Chemical Structure and the Immunostimulating Activity of High–Molecular–Weight Polysaccharides", p. 17.

Primary Examiner—Gary L. Kunz
Assistant Examiner—Kathleen Kahler Fonda
Attorney, Agent, or Firm—Dressler, Goldsmith, Milnamow & Katz, Ltd.

[57] ABSTRACT

The present invention relates to a D 25 polysaccharide compound whose lipid has been partially removed and to its derivatives, wherein at least 85% by weight, preferably 90% of the compound, exists in aqueous solution in monomeric form. The 30 kD molecular weight polysaccharide compound extracted from the membrane proteoglycan of the bacterium *Klebsiella pneumoniae* is mentioned in particular. The amount of palmitic fatty acids which is bound to it in esterified form does not exceed 0.01% by weight of the compound and the amount of palmitic fatty acids which is associated with it in the free form does not exceed 0.1% by weight of the compound.

7 Claims, 1 Drawing Sheet

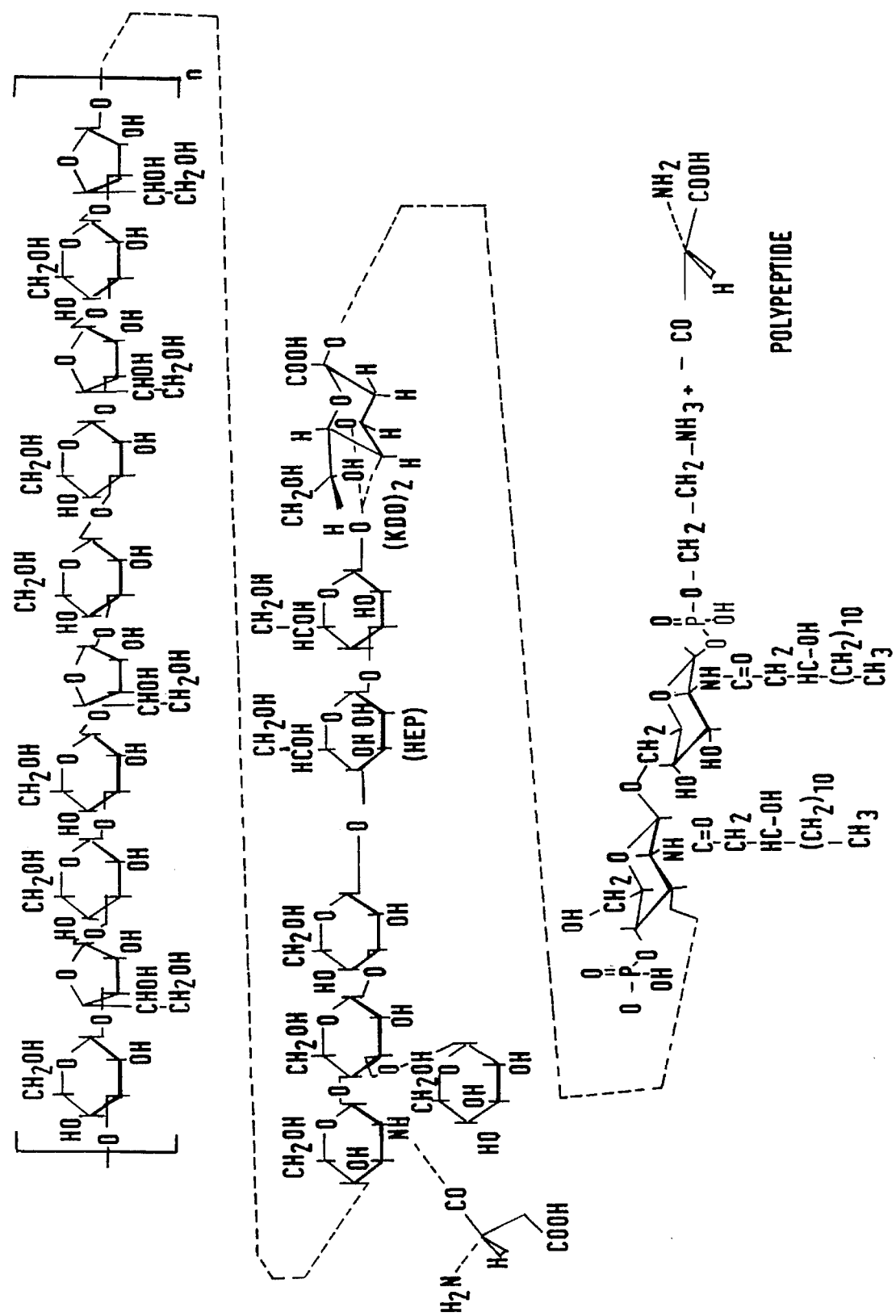

PARTIALLY DELIPIDATED D25 POLYSACCHARIDE COMPOSITION FOR IMAGING AND DIAGNOSIS

This application is a continuation of application Ser. No. 08/192,833, filed Feb. 7, 1994, now abandoned, which is a continuation application of Ser. No. 08/054,347, filed on Apr. 27, 1993, now abandoned, which is a continuation application of Ser. No. 07/666,805, filed Mar. 8, 1991, now abandoned.

$$[PS] \longrightarrow \alpha\,Glc\,p\,NH_2 \xrightarrow{1,3} \alpha\,Glc\,p \xrightarrow{1,4} \alpha\,Gal\,p \xrightarrow{1,3} \alpha\,Hep\,p \xrightarrow{1,3} \alpha\,Hep\,p \xrightarrow{1,5}$$

$$Man\,Oc.\,A \longrightarrow \qquad \uparrow 3,1$$

$$\alpha\,Glc\,p$$

The present invention relates to novel derivatives of the compound termed D 25. It relates specifically to lipid-free derivatives of the compound D 25. The present invention also relates to a process for the preparation of these novel derivatives.

The present invention also relates to compositions containing said derivative which are intended for the imaging, the diagnosis or the therapy in particular of infectious, inflammatory and tumoral loci, through the targeting of macrophages. It concerns injectable compositions which are administrable by the lymphatic route, particularly subcutaneously, or by the intradermic or intrapleural route, or by the i.v. route respectively, but also aerosol compositions.

The present invention also relates to diagnostic kits which permit compositions in accordance with the invention, in which the lipid-free D 25 derivative is labeled with a detectable element, to be reconstituted.

The product termed D 25 is a polysaccharide compound extracted from bacterial membrane proteoglycan. The polysaccharide compound was originally described in the French Patent Applications No. 84 13844 and No. 86 06765.

This D 25 polysaccharide compound is preferably isolated from a non-capsulated and non-pathogenic mutant strain of *Klebsiella pneumoniae* biotype A, held in the National Collection of the Pasteur Institute under the number 145-I-IP.

In the French Patent Applications No. 84 13844 and No. 86 06765, D 25 and its derivatives were presented as possessing immunostimulant properties, particularly toward the induction of endogenous interferon and the activation of NK cells (natural killers).

In these patent applications, the D 25 described contains on the one hand a linear polysaccharide chain consisting of about 5 repeats of a monomeric motif of 10 sugars, and on the other a unique linkage sequence, more complex, to which short peptide chains are attached.

The monomeric repeat unit of the linear polysaccharide chain contains only galactose in the pyran and furan forms in the following proportions:
3 β Gal p, 3 α Gal p, 2 β Gal f, 2 α Gal f.

The sequence of this monomeric unit is as follows:

$$[PS] = \ldots \longrightarrow \beta\,Gal\,p \xrightarrow{1,3} \beta\,Gal\,f \xrightarrow{1,3}$$

-continued $$\alpha\,Gal\,p \longrightarrow \beta\,Gal\,p \xrightarrow{1,3} \alpha\,Gal\,f \xrightarrow{1,3}$$

$$\alpha\,Gal\,p \xrightarrow{1,3} \alpha\,Gal\,f \xrightarrow{1,3} \beta\,Gal\,p \xrightarrow{1,3}$$

$$\alpha\,Gal\,p \xrightarrow{1,3} \beta\,Gal\,f \xrightarrow{1,3}_{n} \quad \text{linkage structure.}$$

The unite linkage structure is fixed to the terminus of the linear polysaccharide chain. It contains glucose, galactose, glucosamine, heptose and mannodeoxyoctulosonic acid residues. Two short peptide chains are attached to this structure.

The presumed sequence is the following:

The following amino acids which constitute the two combined peptide chains occur on average in the following number:

Aspartic acid: 3

Glutamic acid: 2

Serine: 1

Proline: 1

Glycine: 1.5

Alanine: 2

Valine: 1

Leucine: 1

Lysine: 1

Abbreviations:

β Gal p=β galactopyranose

α Gal p=α galactopyranose

β Gal f=β galactofuranose

α Gal f=α galactofuranose

α Glc p=α glucopyranose

α Glc p, $NH_2$=α glucosamine

α Hep p=α heptose (D. mannoheptose)

Man Oc. A=3-deoxy-D-mannooctulosonic acid

Derivatives of D 25 of the amide, ester or ether type, as well as the salts and quaternary ammonium derivatives which are hemisynthesis derivatives of D 25, have been described in the French Patent Applications No. 86 06765 and No. 87 05690 in the name of the Applicant.

Oxidized derivatives of D 25 in which the galactofuranose (Gal f) residue of the linear polysaccharide chain of D 25 has been converted to arabinose, have also been described in the Patent Application No. 87 05690.

The compound D 25 and its derivatives exhibit an affinity for macrophages and constitute an ideal vector agent for recognizing and binding to inflammatory and tumoral foci which mobilize macrophages in their immediate vicinity. As prepared prior to the present invention, only aerosol compositions could be obtained for medical imaging. The use of radiolabeled and aerosol-administered D 25 permits the imaging of inflammatory and tumoral ganglions in man particularly in bronchial cancer ganglion metastases or malignant melanoma ganglion metastases. The trials conducted have in fact demonstrated that any other route for administering the D 25 as prepared in the prior patent applications besides the aerosol route did not result in any satisfactory result for the imaging.

As described in the prior patent applications in the name of the Applicant, the process for the manufacturing of D 25 in fact yields a product on which two β-hydroxymyristic acids representing about 1.5% of the weight of D 25 are grafted through N-glycosidic bonds, and to which traces of $C_{16}$ fatty acids (palmitic) representing about 0.5% of the weight of D 25 are associated in esterified form or in free form.

It is the presence of these fatty acids which gives the molecule its amphipathic character which allows it, by the aerosol route, to penetrate the pulmonary barrier by fusing with the alveolar surfactant without requiring the presence of liposomes or without requiring the use of other galenic forms. The $C_{16}$ free fatty acids fulfill the role of a lipophilic excipient. The presence of a hydrophobic pole on the molecule also plays an important role in the interaction with the monocyte and macrophage membranes so as to allow the D 25 receptor access and its binding to these cells.

Nevertheless, it has been discovered that the strongly lipophilic character of a terminus of the molecule causes, due to the hydrophobic interactions to which it is subjected in aqueous medium, the formation of "polymers" of an apparent molecular weight higher than 150 kD. These "polymeric" forms are in equilibrium, in D 25 solutions, with the 30 kD monomeric form and can represent up to 30% by weight. In this context, "polymer" preferably is understood as micelle type associations or aggregates.

By the aerosol route, these "polymers" are dissociated in the alveolar surfactant and release the monomer which then penetrates the pulmonary barrier. On the other hand, by the intravenous route, these polymers are very rapidly taken up by the reticulo-endothelial system of the liver and of the spleen where they remain bound. This explains the failure of trials which were carried out up until now using compositions that are injectable by the i.v. route. The aerosol route, although allowing pathological foci in the millimeter size range to be revealed, nevertheless has the disadvantage of making it impossible to explore certain anatomic regions which are contaminated either directly by the administration of the radio-aerosol (facial mass) or by the unavoidable presence of the product in the digestive tracts as a result of deglutition or pulmonary mucociliary clearance. Moreover, the administration of a radio-aerosol presents problems for the large-scale use of such a diagnostic form given the precautions that have to be taken in order to avoid the risk of false positive results linked to cutaneous contaminations by the patients themselves.

In the case of the compositions which are injectable by the lymphatic route, the current techniques for imaging the lymphatic system generally employ, in the case of radiography, the injection of contrasting agents by the subcutaneous or intra lymphatic route and, in the case of lymphoscintigraphy, the subcutaneous injection of radio labeled colloids or micro particles which are taken up by the lymphatic flow and then concentrated, by a phenomenon of filtration, inside the ganglions whose visualization they permit.

Lymphoscintigraphy permits the qualitative and quantitative study of the lymphatic drainage (traumatology) and the imaging of ganglions in infectious, inflammatory and tumoral pathologies. In the two latter cases, the limitations of the technique consist in the reduction of the porosity for the lymphatic flow of the invaded ganglions. As a result, a passive concentration, by sieving of the radiolabeled products, is obtained in the first pathological ganglion which is visualized, but the imaging of subsequent stages becomes impossible as a result. Because such pathological structures nevertheless retain some permeability to the lymphatic flow, a new approach to imaging using labeled molecules may be considered if the latter are soluble and highly diffusible. This has led some authors, in recent years, to use radiolabeled serum albumin for the anatomic visualization of the lymphatic routes, or monoclonal antibodies specifically directed against lymphocytes or tumor cells. In the latter case are again found however the well known limitations of immunoscintigraphy which are linked to the low clearance of the compounds employed which hampers the imaging of pathological loci in the sub-millimeter size range.

The existence of a macrophage population which is present in normal ganglions and which is greatly augmented during inflammation or tumor proliferation has led to the use of D 25 as a targeting agent for this cell type by locoregional administration thus allowing a maximum sensitivity of the detection.

The use of D 25 could palliate the disadvantages of the abovementioned macromolecular compounds. However, when it exists in the "polymeric" form, the disadvantage of colloidal or nanoparticulate agents including the blockage at the level of the first ganglions and the impossibility of accessing the entire lymphatic chain is again found.

The aim of the present invention is to provide compositions based on D 25 which are injectable either by the i.v. route or by the lymphatic route and which are intended for the imaging, the diagnosis or the therapy in particular of infectious, inflammatory and tumor loci through the targeting of macrophages.

To achieve this, the present invention thus provides a novel lipid-free D 25 derivative so as to reduce the degree of polymerization of the D 25 in aqueous solution by means of reducing the hydrophobic character of the D 25 without however completely eliminating it, which could destroy the properties of the product with respect to its activity such as its specific binding to the macrophages.

The process for the preparation of D 25 as described in the prior patent applications is characterised in that using a Gram-negative bacterial strain, such as *Klebsiella pneumoniae*, the water soluble proteoglycans are extracted from the membranes. The polysaccharide compounds are isolated after removing the proteins which are present. The soluble proteoglycan is prepared by solubilizing the crude membrane proteoglycan by alkaline hydrolysis. The crude membrane proteoglycan is obtained by centrifugation from a cell homogenate.

Study of the hydrolysis conditions has made it possible to set the limits that are not to be exceeded so as to preserve the properties of D 25, namely a molarity of between 0.3 and 1M in the case of sodium hydroxide, preferably 0.5M, the treatment being continued preferably with stirring at a temperature lower than 90° C., preferably between 50° and 60° C., for example 56° C., the treatment being continued for example for 1 hour. In order to remove excess reagents, the suspension is neutralized using an acid, for example hydrochloric acid, after cooling. Proteins of a molecular weight close to that of the polysaccharide compound are removed by enzymatic hydrolysis of said proteins, in particular by proteinase action. Finally, the D 25 polysaccharide compound is separated by centrifugation after its insolubilization by precipitation.

It has been discovered according to the present invention that the role of the alkaline hydrolysis is not only to solubilize the crude bacterial membrane fraction, particularly of *Klebsiella pneumoniae*, but also to de-esterify, at least partially, $C_{16}$ palmitic fatty acids which are esterified with β-hydroxymyristic acids bound to the polysaccharide chain. But these $C_{16}$ free fatty acids, although they are not bound to it, remain in any case associated with the D 25 if they are not extracted.

It has been discovered according to the present invention that by de-esterifying and extracting the $C_{16}$ palmitic fatty acids, it was possible to obtain a less hydrophobic product which practically no longer leads to the formation of micelles or polymers in aqueous solution and which even leaves practically only the monomeric form if desired.

The hydrophobicity of the compound then is essentially only due to the β-hydroxymyristic acids which are enough to produce the activity and targeting properties of the compound.

If a sufficiently exhaustive alkaline hydrolysis is not carried out, part of the $C_{16}$ fatty acids remain esterified with the β-hydroxymyristic acids. Similarly, if an exhaustive extraction of the free fatty acids is not carried out after alkaline hydrolysis, they reassociate in an esterified form or remain associated in a non-bound manner to the D 25 and cause the formation of micelles or polymers. This is why the D 25, as was described in the prior patent applications, contained from 20 to 30% by weight of the polymeric form in aqueous solution, to the extent that no extraction of these fatty acids was carried out.

The subject of the present invention is therefore a D 25 compound whose lipid has been partially removed, in monomeric form, or whose degree of "polymer" in aqueous solution does not exceed 15%, preferably 10% by weight. In other words, at least 85% by weight, preferably 90% of the compound exists in aqueous solution in monomeric form.

By thus controlling the formation of "polymers" and therefore by modulating the hydrophobic character of the molecule, administration by the intravenous route and by the lymphatic route is made possible.

Thus it appears that, in order to avoid the hepatosplenic binding of the D 25 administered by the intravenous route, it is essential not to exceed 15% of the polymeric form and preferably to stabilize the 30 kD monomeric form. In the case of lymphoscintigraphy, the presence of a certain proportion of polymer (about 10% and up to 15%) is not a disadvantage because it delays the removal of the product and makes it possible to visualize the non-binding ganglions (healthy ganglions), whereas the compound remains bound inside the pathological ganglions.

Finally, the use of a lipid-free D 25 which exists in aqueous solution with a reduced degree of "polymerization" is also an advantage for administration by the aerosol route, the imaging being able to be carried out more rapidly.

In a preferred embodiment of the invention, the compound D 25 according to the invention is extracted from the membrane proteoglycan of the bacterium *Klebsiella pneumoniae* with a molecular weight of 30 kD in the monomeric form.

In particular, the subject of the present invention is a compound which comprises a linear polysaccharide chain composed of the repetition of a sequence containing only galactoses at the terminus of which is found a unique linkage structure containing glucose, galactose, glucosamine, heptose and mannodeoxyoctulosonic acid residues, two short peptide chains are bound to this structure and at the terminus of this structure are grafted two β-hydroxymyristic acids, representing about 1.5% by weight of the compound, through N-glycosidic bonds to two glucosamines of said structure respectively.

In the compounds according to the invention, preferably the amount of palmitic fatty acids which is bound to them in esterified form does not exceed 0.01% by weight of the compound and the amount of palmitic fatty acids which is associated with them in the free form does not exceed 0.1% by weight of the compound. In the present application there is understood by lipid-free D 25, a D 25 whose lipid has been partially removed to the extent that β-hydroxymyristic fatty acids remain bound on the one hand and low amounts of $C_{16}$ fatty acids subsist as mentioned above.

The present invention also provides a process for the preparation of this lipid-free D 25 derivative, wherein:

a) the crude membrane proteoglycan is extracted from bacterial lysates of a Gram-negative bacterial strain, b) the crude proteoglycan of step a) is solubilized by alkaline hydrolysis and the soluble proteoglycan which is present in the aqueous solution is recovered, c) a polysaccharide compound is isolated and if necessary the proteins which are present in the isolated fraction are removed, d) the free fatty acids associated with said polysaccharide compound are extracted using a suitable organic solvent.

Among the Gram-negative bacteria which could be used are *Klebsiella pneumoniae, Serratia marcescens* and *Escherichia coli;* and in particular, as has been seen, *Klebsiella pneumoniae* which is the subject of a deposition in the National Collection of Microbial Cultures (CNCM) under No. 145-I-IP.

In a particular embodiment of the process of the invention, the following steps are carried out:

a) the crude membrane proteoglycan is extracted from a Gram-negative bacterial strain. This crude proteoglycan is recovered in the supernatant obtained after centrifugation of the bacterial lysates.

b) the crude proteoglycan obtained in step a) is solubilized by alkaline hydrolysis, in particular with an alkaline hydroxyl, preferably sodium hydroxide of molarity between 0.3 and 1M, preferably from 0.5 to 0.75M at a temperature lower than 90° C., preferably between 50° and 60° C., for example 56° C., preferably with stirring, the treatment being continued for at least 1 hour.

c) after cooling, the suspension is neutralized with an acid, for example hydrochloric acid, and if necessary an enzymatic hydrolysis of the proteins present in the solution is carried out, in particular by the action of proteinase.

d) the D 25 polysaccharide compound is then purified by alcohol precipitation and recovered for example by centrifugation.

e) the free fatty acids are extracted with a suitable organic solvent for example chloroform or a mixture of chloroform and methanol, then for example the precipitate of the D 25 polysaccharide compound is dispersed in the organic solvent with stirring, then the solvent is removed and finally the precipitate is rinsed with the same solvent.

f) the precipitate is resuspended in water, and the solution of lipid-free D 25 according to the invention is clarified by centrifugation, then the supernatant is recovered, and finally g) the lipid-free D 25 compound according to the invention is isolated by a conventional fractionation or ultrafiltration process.

In particular in step g) a dialysis using distilled water is carried out by ultrafiltration on a membrane with a 10,000 dalton cut-off.

In one embodiment of the process of the invention, which is useful for obtaining in particular a very low degree of "polymerization", in particular lower than 2%, after step f) a new alkaline hydrolysis is carried out, then, after cooling, the suspension is neutralized with an acid, for example hydrochloric acid, and sodium deoxycholate is optionally added to the solution in a proportion not exceeding 0.5%, then the polysaccharide compound is precipitated and the precipitate is suspended in water, and then the lipid-free D 25 compound obtained is isolated by fractionation or ultrafiltration.

The approximately 30 kD monomeric structure of the lipid-free D 25 extracted from the bacterium *Klebsiella pneumoniae* according to the invention is represented in FIG. 1.

The unique linkage structure attached to the terminus of the linear polysaccharide chain contains, in addition to the sequence previously indicated, two terminal glucosamines on each of which a β-hydroxymyristic acid is bound through an N-glycosidic bond. Another peptide chain is bound to the last glucosamine through an ethyl aminophosphate group. The short peptide chains end with an aspartic acid. A peptide chain is bound to the first glucosamine which is adjacent to the PS monomeric unit.

Finally, the present invention relates to compositions which are intended for imaging, diagnosis or therapy which comprise the D 25 compound whose lipid has been partially removed according to the invention.

In a preferred embodiment of the invention, the compositions are intended for the imaging and the diagnosis or the therapy of infectious, inflammatory and tumoral foci through the targeting of macrophages.

The compositions according to the invention may be injectable by the i.v. route, by the lymphatic route, in particular subcutaneously or intrapleurally respectively, or administrable by the aerosol route.

When the compositions are intended for imaging and diagnosis, the polysaccharide compound according to the invention may be labeled with a detectable element such as a paramagnetic radioactive or fluorescent element.

Said polysaccharide compound may also be indirectly detectable, that is to say that it may be detected through a substance which is itself labeled with a detectable element as mentioned previously, said substance recognizing and binding specifically to said polysaccharide compound (lipid-free D 25). By way of a substance which recognizes and binds specifically to said lipid-free D 25 polysaccharide compound, an antibody raised against said compound may be mentioned.

The kits for in vivo or ex vivo imaging or diagnosis according to the invention will therefore contain either the lipid-free D 25 polysaccharide compound and means for labeling it, or the lipid-free D 25 polysaccharide compound and a substance which recognizes said compound and means for labeling said substance.

A field of application of the D 25 derivative described according to the present invention is the scintigraphic imaging or the operative detection when this agent is coupled with a radioactive isotope. These radionuclides may in fact be detectable by visualization or by operative counting using a manually guided probe. It relates then to a diagnosis by counting and not by imaging. By way of a suitable radioactive element according to the invention, a radionuclide which is detectable by scintigraphy such as technetium $^{99m}$Tc or non-limitatively $^{123}$iodine and $^{111}$indium may be mentioned.

The lipid-free D 25 derivative may also be combined with a paramagnetic agent such as gadolinium, for example, in order to form a contrasting product in magnetic resonance imaging (MRI).

In addition to the possibilities of imaging infectious, inflammatory or tumor foci, the lipid-free D 25 constitutes an organ marker for normal or pathological liver and spleen.

More particularly, the injectable compositions containing the lipid-free D 25 with a degree of polymerization lower than 15%, preferably from 5 to 15%, are particularly suitable for the imaging, the diagnosis and the therapy of infectious, inflammatory and tumoral foci of the lymphatic routes through the targeting of macrophages.

A new lymphoscintigraphic application of the compound according to invention concerns the imaging of mediastinal ganglions.

Similarly, the injectable compositions containing the lipid-free D 25 with a degree of polymerization lower than 5% are the most suitable for the imaging, the diagnosis and the therapy of infectious, inflammatory and tumoral foci by the i.v. route through the targeting of macrophages.

Finally, considering its properties which allow the targeting of macrophages, the compound according to the invention may of course be used for therapeutic purposes as transporting agent for the targeted radiotherapy, for the transport of cytotoxic compounds or for the transport of immunogen and/or immunomodulating agents.

Finally, the lipid-free D 25 according to the invention, by virtue of its intrinsic immunopharmacological properties (macrophage activator, interferon-α inducer, NK cell activator, inducer of the production of interleukin-1, and the like), may also be directly used as a medicament, particularly as an immunostimulating agent, against intracellular metastases and infections in particular.

The present invention also relates to lipid-free D 25 derivatives; it concerns oxidized derivatives, the D 25 oxidized derivatives meaning compounds in which the galactofuranose residues (Gal f) of the linear polysaccharide chain have been converted to arabinose; and the derivatives of the amide, ester or ether type, as well as their salts and quaternary ammonium derivatives.

Other characteristics and advantages of the present invention will emerge from the following examples.

BRIEF DESCRIPTION OF THE FIGURE

FIG. 1 represents the structure of the lipid-free D 25.

EXAMPLE 1: MANUFACTURING PROCESSES
(Given Using 1 kg of *K. pneumoniae* Biomass Expressed Dry Weight)

1. Preparation of Clarified Bacterial Lysates

The *Klebsiella pneumoniae* biomass is obtained by culture in a fermenter in liquid medium under conventional conditions. The only specific constraint is the abrupt termination of growth by cooling to +4° C. at the end of the exponential growth phase so as to preserve the integrity of the biological structures.

The biomass is separated from the culture medium by continuous centrifugation in the cold in an industrial separator of the Sharples or Westfalia types. After washing by resuspending in solution in sterile physiological serum and centrifuging, the cell concentrate is stored frozen while waiting to be processed.

The bacterial concentrate is thawed in a reactor and suspended in Tris-HCl buffer (10 mM) pH 7.0 containing $MgCl_2$ (10 mM) and NaCl (0.15 mM) at 4° C. so as to obtain a final concentration equivalent to 50 g of dried cells per liter of suspension. 5 mg of DNase are next added per liter of suspension.

The microbial cells are then disintegrated by passing in a continuous manner through APV Manton Gaulin type industrial mills. The bacterial lysate thus obtained is subjected to a first continuous clarification at 15,000× g in a Sharples separator at 4° C. so as to remove the grinding residues and the non-ground cells. Once the centrifugation pellet is removed and the supernatant recovered, it constitutes the clarified lysate.

2. Preparation of Membrane Proteoglycan

The clarified bacterial lysate is acidified to pH 4.2±0.2 with acetic acid and allowed to stand for 30 minutes at +4° C. The precipitate consisting of impurities which is formed is removed by continuous centrifugation at 15,000× g in a Sharples. The opalescent supernatant containing the membrane proteoglycan is neutralized with NaOH, then dialysed by ultrafiltration at constant volume against distilled water on a membrane with a 10,000 dalton cut-off. When the resistivity is equal to or greater than $1000\Omega cm^{-1}$ the volume is concentrated by filtration on a 10,000 dalton membrane to 6 l for the equivalent of 1 kg of dry cells of the initial biomass.

The protein content of the membrane proteoglycan suspension is determined by the biuret reaction then adjusted by dilution with distilled water to obtain a final concentration of 10 mg of protein per ml.

This *K. pneumoniae* membrane proteoglycan suspension will then be used for the extraction of D 25 for the purpose of its various applications.

3. Preparation of Lipid-free D 25 for use in Lymphoscintigraphy (About 10% of the Compound in the "Polymer" Form in Aqueous Solution) (Code SJD252)

To the suspension of membrane proteoglycan obtained in 1.2, concentrated sodium hydroxide is added to a final normality of 0.5 to 0.75N (preferably 0.5N). The solution is then brought to 56° C. and maintained with stirring for 1 hour at this temperature. After cooling to room temperature, the solution is neutralized with hydrochloric acid.

To the neutralized solution is added Tris q.s. to M/100 and EDTA q.s. to M/1000, and the pH is adjusted to 7.4. An enzymatic digestion is then carried out for 2 hours at 37° C. in the presence of 0.4 g/l of proteinase K and 0.1 g/l of lysozyme.

The D 25 is separated by precipitating with 2 volumes of ethanol previously cooled to 20° C. After allowing to stand for 30 minutes at 4° C., the precipitate is recovered by continuous centrifugation on a Sharples with a flow rate of 6 l/minute.

The D 25 pellet is immediately dispersed in 1 l of a chloroform:methanol (3:1) mixture by passing through a Turrax at room temperature, filtered on a No. 3 sintered glass and the precipitate rinsed on the filter with 500 ml of the same chloroform:methanol mixture. The precipitate is dried under a stream of nitrogen then resuspended in 1.5 l of distilled water by dispersing with a Turrax, and maintained with stirring for 1 night at +4° C.

The lipid-free D 25 solution is clarified by centrifuging at 30,000 g for 60 minutes at +4° C., and the supernatant is dialysed against distilled water using membranes with a 10,000 dalton cut off, until a resistivity equal to or greater than $5000\Omega cm^{-1}$ is obtained. The volume is adjusted to 1.5 l with distilled water and the pH adjusted to 7.2.

The D 25 is then sterilized by filtration on a 0.22 µm membrane and freeze-dried under sterile conditions. This freeze-dried compound constitutes the SJD252, the principle which is used below for lymphoscintigraphy.

4. Preparation of D 25 for Intravenous Injection (Code SJD253) (Less than 5% of the Compound in the "Polymer" Form in Aqueous Solution)

To the suspension of membrane proteoglycan obtained in 1.2, concentrated sodium hydroxide is added so as to obtain a final normality of 0.5 to 0.75N (preferably 0.75N). The solution is then brought to 56° C. and maintained with stirring for 1 hour at this temperature. After cooling to room temperature, the solution is neutralized with hydrochloric acid.

To the neutralized solution is added Tris q.s. to M/100 and EDTA q.s. to M/1000, and the pH is adjusted to 7.4. An enzymatic digestion is then carried out for 2 hours at 37° C. in the presence of 0.4 g/l of proteinase K and 0.1 g/l of lysozyme.

The D 25 is separated by precipitating with 2 volumes of ethanol previously cooled to 20° C. After allowing to stand for 30 minutes at +4° C., the precipitate is recovered by continuous centrifugation on a Sharples with a flow rate of 6 l/minute.

The D 25 pellet is immediately dispersed in 2 l of a chloroform:methanol (3:1) mixture by passing through a Turrax at room temperature with intermittent stirring for 15 minutes. The solvent is then removed by being filtered on a No. 3 sintered glass and the precipitate rinsed on the filter with 1 l of the same chloroform:methanol mixture. The precipitate is dried under a stream of nitrogen then resuspended in 1.5 l of distilled water by dispersing with a Turrax, and maintained under stirring for 1 night at +4° C.

The lipid-free D 25 solution is clarified by centrifuging at 30,000× g for 60 minutes at 4° C., and the supernatant is recovered, then concentrated sodium hydroxide is added so as to obtain a final normality of 0.5N. The solution is then brought to 56° C. and maintained with stirring for 1 hour at this temperature. After cooling to room temperature, the solution is neutralized with hydrochloric acid.

Sodium deoxycholate q.s. to 0.5% is added to this solution, it is then vigorously stirred at 25° C. for 30 minutes. Two volumes of ethanol previously cooled to +4° C. are added so as to precipitate the D 25. After allowing to stand for 30 minutes at 4° C., the precipitate is recovered by continuous centrifugation in a Sharples with a flow rate of 6 l/minute.

The D 25 pellet is immediately resuspended in 2 l of distilled water by dispersing with a Turrax, then maintained with stirring for 1 night at +4° C. The solution is dialysed against distilled water using membranes with a 10,000 dalton cut-off until a resistivity equal to or greater than $5000\Omega cm^{-1}$ is obtained. The volume is adjusted to 1.5 l with distilled water and the pH adjusted to 7.2.

The D 25 is then sterilized by filtration on a 0.22 µm membrane and freeze-dried under sterile conditions.

This freeze-dried compound constitutes the SJD253, the principle which is used below for the intravenous route. D 25 extraction schemes for the various scintigraphic imaging applications Using a *Klebsiella pneumoniae* membrane proteoglycan suspension adjusted to 10 mg/ml of protein and for 1 kg of initial biomass (expressed as dry weight)

I—D 25:SJD251 (about 20 to 30% of polymer) (prior processes)
1. Alkaline hydrolysis (0.5N NaOH—1 hour at 56° C.)
2. Neutralization
3. Enzymatic digestion (0.1 g/l proteinase K+0.1 g/l lysozyme for 2 hours at 37° C.)
4. Alcohol precipitation (2 volumes of ethanol at 20° C.)
5. Resuspended in 0.5M $CH_3COONa$
6. Alcohol precipitation (id. 4)
7. Resuspended in distilled water
8. Clarification (60 min. at 30,000 g)
9. Dialysis against $H_2O$ ($\geq 2,500 \Omega cm^{-1}$ using a 10,000 D membrane)
10. Sterilization on a 0.22 μm membrane
11. Sterile freeze-drying: SJD251.

II—D 25 for lymphoscintigraphy:SJD252 (about 7–12% of polymers)
1. Alkaline hydrolysis (0.5N NaOH—1 h at 56° C.)
2. Neutralization
3. Enzymatic digestion (0.4 g/l proteinase K+0.1 g/l lysozyme for 2 hours at 37° C.)
4. Alcohol precipitation (2 volumes of ethanol at 20° C.)
5. Lipid removal with chloroform:methanol. Drying
6. Resuspended in distilled water (1 night at 4° C.)
7. Clarification (60 min. at 30,000 g)
8. Dialysis against $H_2O$ ($\geq 5,000 \Omega cm^{-1}$ using a 10,000 D membrane)
9. Sterilization on a 0.22 μm membrane
10. Sterile freeze-drying: SJD252.

III—D 25 by intravenous route:SJD253 (practically monomeric, degree of polymer<5%)
1. Alkaline hydrolysis (0.75N NaOH—1 hour at 56° C.)
2. Neutralization
3. Enzymatic digestion (0.4 g/l proteinase K+lysozyme at 20° C.)
4. Alcohol precipitation (2 volumes of ethanol at 20° C.)
5. Lipid removal with chloroform:methanol. Drying
6. Resuspended in distilled water (1 night at 4° C.)
7. Clarification (60 min. at 30,000 g)
8. Alkaline hydrolysis (0.5N NaOH—1 hour at 56° C.)
9. Neutralization
10. Na deoxycholate treatment (0.5%—30 minutes at 25° C.)
11. Alcohol precipitation (2 volumes of ethanol at 4° C.)
12. Resuspended in distilled water (1 night at 4° C.)
13. Dialysis against $H_2O$ ($\geq 5,000 \Omega cm^{-1}$ using 10,000 D membrane)
14. Sterilization on a 0.22 μm membrane
15. Sterile freeze-drying: SJD253.

EXAMPLE 2: COMPOSITIONS INTENDED FOR THE IMAGING AND DIAGNOSIS OF INFECTIOUS, INFLAMMATORY AND TUMOR FOCI, THROUGH THE TARGETING OF MACROPHAGES

The lipid-free D 25 according to the invention and its derivatives have proven to possess an affinity for monocyte - macrophage type cells which make them more particularly an ideal transporting agent for recognizing and binding to the inflammatory and tumor foci mobilizing these cells.

Binding studies of lipid-free D 25 labeled with fluorescein isothiocyanate (D 25-FITC) were carried out on human leucocytes and on different types of cell lines. At a dose of 0.1 to 1 mg/ml, the D 25-FITC incubated in the presence of human monocytes, lymphocytes and ganulocytes shows by flow cytofluorimetry an elective binding to the monocyte population. The curves representing the evolution of the binding of D 25-FITC to these cells as a function of its concentration in the medium show a preferential affinity of monocytes for the lipid-free D 25 in the 0.5–10 mg/ml concentration range with a 2.2 to 6.5-fold increase in the fluorescence index for the monocytes (1.1 to 1.6 for the lymphocytes and the polynuclears).

The use of various types of cell lines—hematopoietic (K562), promyelocytes (HL-60), monocytes-like (U937), lymphoblasts (IM-9), myelomatous (U-266) and T leukemic (MOLT-4) cells—in studying the specificity of the D 25-FITC binding, by displacement after competition with the non-labeled D 25, confirms the electivity of the binding for the monocyte cell line (Table 1).

TABLE 1

Study of fluorescent lipid-free D 25 binding (fluorescein isothiocyanate) to cell lines of human origin

| Cell type | Mean fluorescence intensity | | |
|---|---|---|---|
| | Background noise | Initial fluorescence* | Fluorescence after competition by non-labeled lipid-free D 25** |
| Monocyte cell line | | | |
| K562 | 2.9 | 5.7 | 3.7 (−71)*** |
| HL-60 | 2.8 | 5.7 | 4.8 (−31) |
| U-937 | 3.1 | 6.6 | 4.5 (−60) |
| Other cell lines | | | |
| IM-9 | 2.8 | 3.6 | 3.4 |
| U-266 | 3.5 | 4.5 | 4.1 |
| MOLT-4 | 3.6 | 3.6 | 3.3 |

*1 mg/ml D 25-FITC
**1 mg/ml D 25-FITC after competition by 10 mg/ml D 25
***Percentage inhibition of the D 25-FITC binding by the D 25.

2.1 Imaging through the Targeting of Macrophages by the i.v. Route

The strategy of in vivo targeting of macrophages by the transporting agent which constitutes the subject of the present invention was evaluated in animals by scintigraphy in two experimental pathology models:
1) immunological arthritis induced in the rabbit by ovalbumin,
2) inflammatory reaction associated with the localized irradiation of the leg muscle in the pig.

Experimental results

1°/Adult New Zealand rabbits were sensitized by ovalbumin combined with Freund's adjuvant, administered by repeated i.d. injections on the back. After one month of sensitization a triggering injection of ovalbumin is carried out in the articulation corresponding to the right knee. After 15 days of progression of the pathology and regression of the initial oedema, the animals are subjected during three months to scintigraphies by SJD253 or methylene diphosphonate (osteo-articular reference tracer) labeled with $^{99m}Tc$ and administered by the i.v. route.

The examinations were carried out with conscious animals using a Phogammacamera (Siemens) equipped with a parallel collimator and connected to a TIM 512 computer system (Medimag, Besançon). A static acquisition of 1 minute with a matrix of 128×128 pixels was carried out one hour after intravenous injection of the products labeled with 1 mCi of $^{99m}TcO_4^-$ (CIS, Gif-sur-Yvette).

The labeling of SJD253 was carried out using 500 µg of sterile and non-pyrogenous product reduced under vacuum by 100 µg of stannous chloride or another stannous tin halide ($SnF_2$ etc.) according to the technique of Lin et al., J. Nucl. Med., 1971, 12, 204–211, using 2 mCi of $^{99m}TcO_4^-$.

The labeling yield determined by thin layer partition radiochromatography in the solvent methanol-water (85/15) is greater than 99.5% without the presence of detectable amounts of colloid.

For the examinations with methylene diphosphonate, a TCK 14M kit (CIS, Gif-sur-Yvette) containing 2.5 mg of methylenediphosphonic acid and 0.25 mg of dihydrated stannous chloride was used. The labeling was carried out extemporaneously by adding 5 mCi of $^{99m}TcO_4^-$. The labeling yield, determined by partition radiochromatography in a methanol/water (85:15) medium was higher than 99.5% without significant detection of colloid. A quarter of the preparation corresponding to an activity of 1 mCi was injected by the intravenous route into the animals one hour before the scintigraphic examination.

2°/Experimentation on the foci of irradiation in pigs

Irradiations using 100 Ci of a $^{192}$iridium source were carried out on the lateral face of the right leg of Large White pigs by delivering an irradiation dose of 60 Gy at a distance of 2 cm. The irradiation is localized at 10 cm behind the femur and equidistant from the trochanter crest and the lateral epicondyl. The animals were operated on 15 days after irradiation, under gaseous anesthesia in order to carry out a resection of the irradiated skin and avoid non-specific inflammatory reactions and an infection induced by radionecrosis. The scintigraphic examinations were carried out 60 to 70 days after the operation, after checking the absence of any oedema or superficial inflammatory reaction connected with the cicatrization process. The examinations were carried out using a GCA type gamma camera (Toshiba) equipped with a parallel collimator and set on the 140 keV photoelectric peak of $^{99m}Tc$ with a window of 20%. The digitizing and storage of the images were carried out using a Pericolor 1000 image analyzer. For a 70 kg animal, the administered dose corresponded to 1 mg of SJD253 labeled with 10 mCi of $^{99m}TcO_4^-$ in the presence of 200 µg of stannous chloride one hour before the scintigraphic examination. After checking the quality of the labeling by thin layer partition radiochromatography according to the procedure previously described, the labeled D 25 was injected by the intravenous route into the marginal vein of the ear one hour before the scintigraphic examination.

2.2 Targeting of macrophages by the lymphatic route

This strategy of macrophage targeting for lymphoscintigraphy was evaluated in healthy animals and in experimental pathology.

1) In healthy dogs and monkeys:

The study was carried out in conscious animals by subcutaneous injection into two interdigital spaces of the posterior paws, of 50 µl per injection site of a solution containing 500 µg of D 25 labeled with 500 µCi of $^{99m}Tc$ in the presence of 100 µg of a stannous tin halide (for example $SnCl_2$, $SnF_2$ etc.) according to the technique of Lin et al. J. Nucl. Med., 1971, 12, 204–211. A calibration test was carried out using radiopharmaceutical products currently marketed for lymphoscintigraphy:human albumin nanocolloids (Nanocoll, Solco, Basle) or colloidal rhenium sulfide (TCK-17, CIS, Gif-sur-Yvette) labeled with $^{99m}$technetium.

The D 25s studied correspond:

— to the natural product termed SJD251,

— to the derivative optimized for lymphoscintigraphy and obtained according to the technique, described in the present patent, for limiting the hydrophobic interactions due to the amphiphilic nature of the natural molecule; the product thus optimized is termed SJD252. The labeling yield of the D 25 fractions was determined by thin layer partition radiochromatography in the solvent methanol/water (85/15) and was higher than 99.5% without the presence of detectable amounts of colloid.

The examinations were carried out on a Phogammacamera (Siemens) equipped with a parallel collimator and connected to a TIM 512 computer system (Medimag, Besançon). Dynamic acquisitions were carried out on the posterior limbs at the rate of one image per minute for 1 hour. The results show practically identical kinetics of the lymphatic distribution of the SJD251, Nanocoll and colloidal rhenium sulfide, characterized by a visualization of ganglionic relays after 30 minutes which lasts up to one hour, or even longer.

For the lipid-free D 25 (SJD252) optimized for lymphoscintigraphy, the takeup by the lymphatic system is extremely rapid from the first five minutes following the injection and the imaging of the ganglionic relays is obtained in 10–20 minutes with a scintigraphic contrast close to the one obtained by the reference radiopharmaceuticals. In contrast in healthy animals, a rapid clearance causing the disappearance of ganglionic images occurs between 30 and 60 minutes after the injection.

In experimental pathology, 2 models were used:

— *Corynebacterium pseudotuberculosis* infection in lambs: the bacterial dissemination from the infectious granuloma situated at the extremity of the posterior limb is carried out by the lymphatic drainage tracts, causing the formation of 2 infectious ganglions which become impermeable to lymphoscintigraphic reference agents.

— A model of reactive inflammatory axillary ganglion induced by i.d. injection of tuberculin in Papio papio monkeys previously immunized with BCG.

In the case of infectious ganglions in sheep, SJD252 allows the imaging of the 2 pathological ganglions in the 30–60 minutes following the injection, with a practically inexistent clearance during at least 90 minutes. In the healthy limb on the opposite side, the examination carried out allows the imaging of normal ganglions for 30 minutes only since the clearance of the non-bound product then intervenes.

For the inflammatory ganglion induced by tuberculin in monkeys, a similar result is obtained within the same period but the image lasts for 3 hours.

A new lymphoscintigraphic application of SJD252 concerns the imaging of mediastinal ganglions. This development has been carried out in conscious Papio papio monkeys by intradermic or intrapleural injection of 250 µg of the product labeled with 250 µCi of $^{99m}$technetium. The pleural clearance of the scintigraphic agent is accompanied in the 3 hours after the injection by an activity which increases with time in the posterior mediastinal ganglions and thus allows their imaging.

The principal zones which are normally explorable by this route are the lower and upper limbs and the ganglionic chains of the mammary region after subcutaneous or intradermic injection of the product in the lymphatic drainage regions. The possibilities of exploration have been extended to the imaging of mediastinal ganglions which are of considerable importance in inflammatory and tumor pathology; it is carried out by intrapleural injection of the product.

We claim:

1. A composition for imaging and diagnosis comprising:
   a physiologically acceptable carrier; and
   a D25 polysaccharide compound, or its amide, ester, ether, oxide, and quaternary ammonium derivatives, or salts thereof, having two β-hydroxymyristic acids bound thereto via an amide linkage, wherein the amount of free and bound palmitic fatty acids is less than about 0.5% by weight of the compound; wherein at least 85% by weight of the compound exists in aqueous solution in monomeric form; and wherein the compound is labeled with a detectable amount of a radioactive, paramagnetic or fluorescent marker.

2. A method of imaging and diagnosing an infectious, inflammatory or tumorous condition in a patient comprising administering to said patient the composition of claim 1 in an amount effective for imaging.

3. The method of claim 2 wherein said administration is by intravenous injection.

4. The method of claim 2 wherein said administration is by lymphatic injection.

5. The method of claim 4 wherein said injection is by the subcutaneous route.

6. The method of claim 4 wherein said administration is by the intrapleural route.

7. The method of claim 2 wherein said administration is by the aerosol route.

* * * * *